(12) United States Patent
Gautreau et al.

(10) Patent No.: US 11,253,346 B2
(45) Date of Patent: *Feb. 22, 2022

(54) APPARATUS AND METHOD FOR A SINGLE SENSOR ACTION PLATE

(71) Applicant: DESVAC, Saint-Barthelemy-d'Anjou (FR)

(72) Inventors: Jeremy Gautreau, Bouchemaine (FR); Stephane Veyrent, Soulaines sur Aubance (FR)

(73) Assignee: DESVAC, Saint-Barthelemy-d'Anjou (FR)

( * ) Notice: Subject to any disclaimer, the term of this patent is extended or adjusted under 35 U.S.C. 154(b) by 300 days.

This patent is subject to a terminal disclaimer.

(21) Appl. No.: 16/379,310

(22) Filed: Apr. 9, 2019

(65) Prior Publication Data

US 2019/0298503 A1 Oct. 3, 2019

Related U.S. Application Data

(63) Continuation of application No. 15/458,508, filed on Mar. 14, 2017, now abandoned.

(51) Int. Cl.
*A61D 1/02* (2006.01)
*A61M 5/20* (2006.01)
(Continued)

(52) U.S. Cl.
CPC ........... *A61D 1/025* (2013.01); *A61M 5/2053* (2013.01); *A61M 5/3158* (2013.01);
(Continued)

(58) Field of Classification Search
CPC . A61D 1/02; A61D 1/025; A61M 2005/2013; A61M 2005/206;
(Continued)

(56) References Cited

U.S. PATENT DOCUMENTS 3,964,481 A * 6/1976 Gourlandt .............. A61D 1/025
604/152
4,276,879 A * 7/1981 Yiournas ................ A61D 1/025
604/154
(Continued)

FOREIGN PATENT DOCUMENTS

CN 104703641 A 6/2015
EP 2698180 A1 2/2014
(Continued)

OTHER PUBLICATIONS

European Office Action dated Sep. 27, 2019 in Patent Application No. 18717985.8, 3 pages.
(Continued)

*Primary Examiner* — Quynh-Nhu H. Vu
(74) *Attorney, Agent, or Firm* — Oblon, McClelland, Maier & Neustadt, L.L.P.

(57) ABSTRACT

A vaccination device can be used to vaccinate day-old chicks. To vaccinate the day-old chicks safely while ensuring vaccination efficacy, the vaccination device can include a vaccination needle configured to extend from the vaccination device at a vaccination delivery location and an action plate. The action plate can be coupled to the vaccination device such that the action plate is positioned next to the vaccination delivery location. The action plate can include an action button, wherein the action button is configured to receive a day-old chick presented to the action plate in a predetermined loading position, receive a press of the action button, and in response to pressing the action button, cause the vaccination needle to extend from the vaccination device at the vaccination delivery location to deliver a subcutaneous injection to the day-old chick.

21 Claims, 12 Drawing Sheets

(51) Int. Cl.
*A61M 5/32* (2006.01)
*A61M 5/315* (2006.01)

(52) U.S. Cl.
CPC ..... *A61M 5/3287* (2013.01); *A61M 2005/206* (2013.01); *A61M 2005/2013* (2013.01); *A61M 2205/8218* (2013.01); *A61M 2250/00* (2013.01)

(58) Field of Classification Search
CPC ...... A61M 2205/8218; A61M 2250/00; A61M 5/2053; A61M 5/3158; A61M 5/3287
See application file for complete search history.

(56) References Cited

U.S. PATENT DOCUMENTS

| | | | | |
|---|---|---|---|---|
| 4,758,227 | A * | 7/1988 | Lancaster, Jr | A61D 1/025 604/144 |
| 4,863,443 | A * | 9/1989 | Hornung | A61D 1/025 604/500 |
| 5,199,952 | A * | 4/1993 | Marshall, Sr | A61D 1/025 604/156 |
| 5,312,352 | A * | 5/1994 | Leschinsky | A61M 5/36 285/924 |
| 5,468,227 | A * | 11/1995 | Haskell | A61D 1/025 119/713 |
| 8,211,058 | B2 * | 7/2012 | Jorna | A61D 1/025 604/131 |
| 2007/0093747 | A1 * | 4/2007 | Smith | A61D 1/025 604/67 |
| 2015/0290392 | A1 * | 10/2015 | Henderson | A61M 5/3204 604/111 |
| 2016/0324613 | A1 * | 11/2016 | Halamish | A61D 1/025 |

FOREIGN PATENT DOCUMENTS

| | | |
|---|---|---|
| EP | 2727617 A1 | 5/2014 |
| RU | 73 191 U1 | 5/2008 |

OTHER PUBLICATIONS

Canadian Office Action dated Nov. 18, 20202 in Canadian Patent Application No. 3,055,876, 3 pages.
International Search Report and Written Opinion dated Jun. 13, 2018, in PCT Application No. PCT/IB2018/000305. filed Mar. 3, 2018.
Combined Chinese Office Action and Search Report dated April 2, 2021 in corresponding Chinese Patent Application No. 2018800235855 (with English Translation), 18 pages.
Combined Russian Office Action and Search Report dated Jun. 9, 2021 in corresponding Russian Patent Application No. 2019132213 (with English Translation), 21 pages.
Canadian Office Action dated Jun. 3, 2021 in Canadian Patent Application No. 3,055,876, 4 pages.
Indonesian Office Action dated Jul. 9, 2021 in Indonesian Patent Application No. P00201908056, 3 pages.
Indian Office Action dated Jul. 20, 2021 in Indian Patent Application No. 201917036932, 6 pages.
Decision on Rejection dated Sep. 28, 2021 in corresponding Chinese Patent Application No. 201880023585.5 (with English translation)(11 pages).

* cited by examiner

APPARATUS AND METHOD FOR A SINGLE SENSOR ACTION PLATE

CROSS-REFERENCE TO RELATED APPLICATIONS

This application is a continuation of U.S. application Ser. No. 15/458,508, filed Mar. 14, 2017, the entire contents and disclosure of which are incorporated by reference herein.

BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Vaccination of animals is a common practice which may assist in the safety of the animals as well as the end consumer. For example, chicks may be vaccinated when they are one day old. A vaccination device can be used to vaccinate the day-old chicks. The vaccination device can be equipped with an action plate which can include a triggering mechanism to deliver the vaccination when activated. It is important that the vaccination is done accurately, safely, and quickly. Potential safety issues that can arise include self-injection of the operator of the vaccination device, as well as incorrect injection locations on the day-old chick.

Current action plates typically include one or two action buttons. With respect to current one button action plates, the location of the action button can have an increased risk of self-injection. Additionally, one button action plates have consistency issues in which there is a risk of injecting a day-old chick with important vaccines at wrong injection locations. The inconsistency can include a wide range of wrong injection locations including upper head, back of the head, side of the head, front of the neck, and the like. Two button action plates, in which both buttons need to be pressed for an injection to be delivered, may not reduce the risk of self-injection as the second button can easily be by-passed in an attempt to maintain an accostomed speed at which the day-old chicks can be vaccinated.

SUMMARY

The foregoing paragraphs have been provided by way of general introduction, and are not intended to limit the scope of the following claims. The described embodiments, together with further advantages, will be best understood by reference to the following detailed description taken in conjunction with the accompanying drawings.

According to aspects of the disclosed subject matter, a vaccination device can be used to vaccinate day-old chicks. To vaccinate the day-old chicks safely while ensuring vaccination efficacy, the vaccination device can include a vaccination needle configured to extend from the vaccination device at a vaccination delivery location and an action plate. The action plate can be coupled to the vaccination device such that the action plate is positioned next to the vaccination delivery location. The action plate can include an action button, wherein the action button is configured to receive a day-old chick presented to the action plate in a predetermined loading position, receive a press of the action button, and in response to pressing the action button, cause the vaccination needle to extend from the vaccination device at the vaccination delivery location to deliver a subcutaneous injection to the day-old chick.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
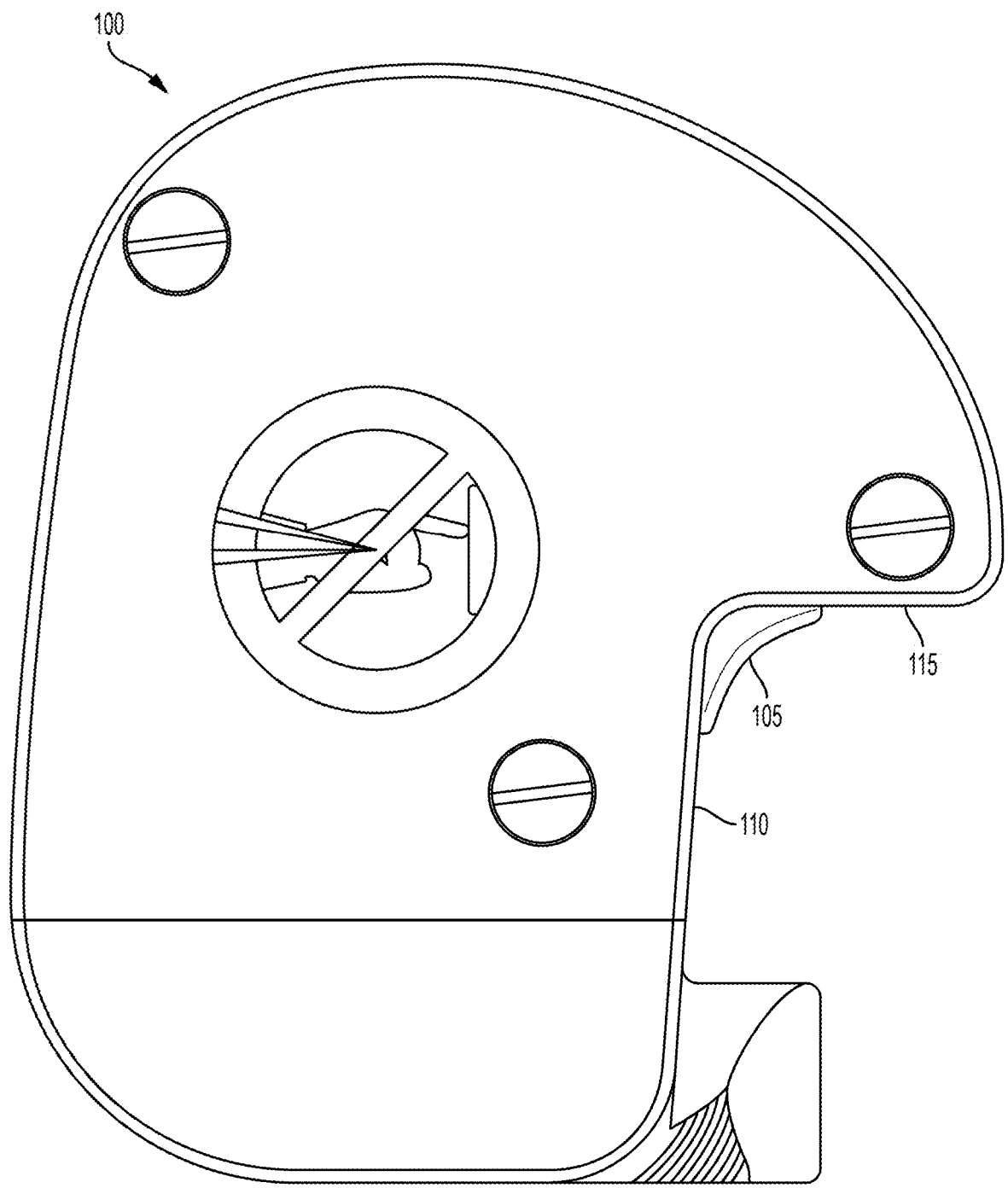
FIG. 1 depicts an exemplary top view of an action plate according to one or more aspects of the disclosed subject matter.

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed subject matter. However, it will be apparent to those skilled in the art that embodiments may be practiced without these specific details. In some instances, well-known structures and components may be shown in block diagram form in order to avoid obscuring the concepts of the disclosed subject matter.

Reference throughout the specification to "one embodiment" or "an embodiment" means that a particular feature, structure, characteristic, operation, or function described in connection with an embodiment is included in at least one embodiment of the disclosed subject matter. Thus, any appearance of the phrases "in one embodiment" or "in an embodiment" in the specification is not necessarily referring to the same embodiment. Further, the particular features, structures, characteristics, operations, or functions may be combined in any suitable manner in one or more embodiments. Further, it is intended that embodiments of the disclosed subject matter can and do cover modifications and variations of the described embodiments.

It must be noted that, as used in the specification and the appended claims, the singular forms "a," "an," and "the" include plural referents unless the context clearly dictates otherwise. That is, unless clearly specified otherwise, as used herein the words "a" and "an" and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein, merely describe points of reference and do not necessarily limit embodiments of the disclosed subject matter to any particular orientation or configuration. Furthermore, terms such as "first," "second," "third," etc., merely identify one of a number of portions, components, points of reference, operations and/or functions as described herein, and likewise do not necessarily limit embodiments of the disclosed subject matter to any particular configuration or orientation.

Referring now to the drawings, wherein like reference numerals designate identical or corresponding parts throughout the several views.

Vaccinating animals, such as day-old chicks, can be an important process in food preparation for the safety of the consumer. Chickens are involved in popularly purchased items including eggs and chicken meat (chicken breasts, chicken wings, chicken legs, etc.). Because of the demand, the speed at which the day-old chicks are vaccinated can be an important first step in the process that may eventually end with a consumer. The speed at which an operator can vaccinate the day-old chicks is impressive. For example, one operator can vaccinate 3000+ chickens per hour. At this rate, the durability of the device, the safety of the operator and the day-old chicks, and the quality and efficacy of the vaccination is important for successful operations. The consistency can be maintained even when the vaccination rate is at a rate of 3000+ vaccinations per hour. A safe and precise vaccination, as well as a long lasting and durable vaccination device, can increase productivity and reduce any down time due to operator injury, malfunctioning devices, inconsistent injection locations, and the like.

FIG. 1 depicts an exemplary top view of an action plate 100 according to one or more aspects of the disclosed subject matter. The action plate 100 can be configured to be part of a vaccination device (FIG. 9) to safely and efficiently vaccinate day-old chicks with high quality and efficacy. The action plate 100 can include an action button 105. The action plate 100 can provide improved safety for both the operator and the day-old chick, while providing a consistent and more precise injection site. The improved safety and efficacy is based on the location of the action button 105. The action button 105 can be disposed in a predetermined location corresponding to where a first outer surface 110 of the action plate 100 and a second outer surface 115 of the action plate 100 connect to form a corner. Alternatively, or additionally, the action button 105 can be positioned a predetermined distance (or a predetermined range of distances) away from a vaccination delivery location. Alternatively, or additionally, the action button 105 can include an activation axis and the activation axis can be at a predetermined angle relative to an axis corresponding to a vaccination delivery location axis. The action button 105 can have a predetermined curve that can assist in receiving a day-old chick, wherein the day-old chick's head can be pressed against the action button as further described herein. Additionally, the action button 105 can be configured to be pressed when a certain amount of pressure is applied at least substantially along an axis of the action button 105. Pressing the action button 105 can cause a chick to be vaccinated, for example, as further described herein. The location of the action button 105 can prevent delivering a vaccination by bypassing the action button 105. Additionally, the location of the action button 105 and the direction that the action button 105 is pressed can reduce a risk of the operator coming into contact with the needle that vaccinates the day-old chick. Further, the action button 105 can have a predetermined thickness to assist in precise loading of the day-old chick in the action plate 100 for vaccination. The action button 105 can have a predetermined thickness in the middle and become progressively thinner toward each end of the action button 105. Further, the curve of the action button can be between 41° and 45° relative to the activation axis.

At least a portion of the action plate 100 can be made of anodized aluminum and the action button 105 can be stainless steel to improve durability, thereby reducing down time due to malfunction and additionally can prevent rust issues. However, a lid/hood can be made of plastic to provide internal access to the action plate 100.

Figure 2:
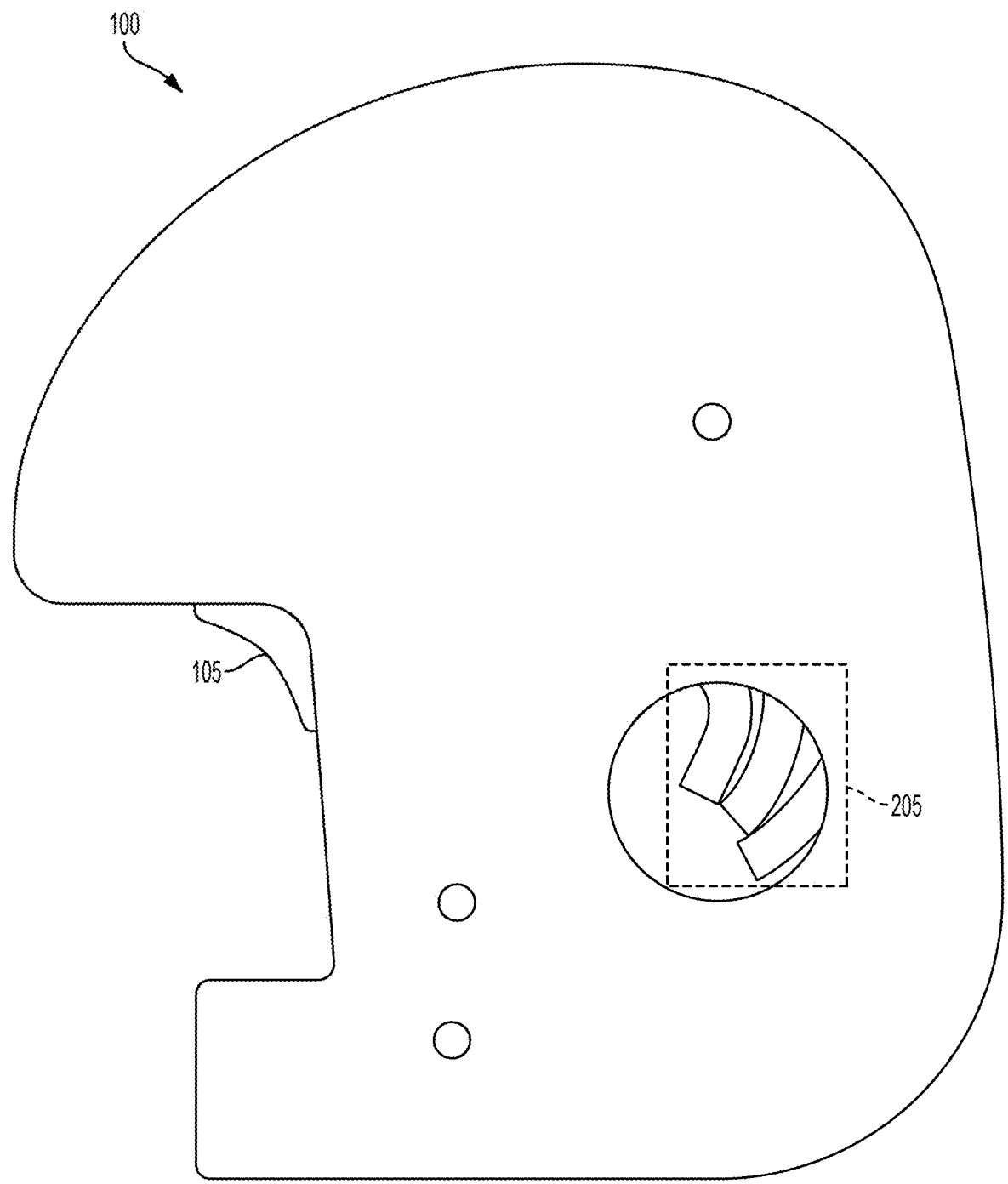
FIG. 2 depicts an exemplary bottom view of an action plate according to one or more aspects of the disclosed subject matter.

FIG. 2 depicts an exemplary bottom view of the action plate 100 according to one or more aspects of the disclosed subject matter. The action plate 100 can include a plurality of connection points 205. The connection points 205 can include a first pipe (sensor air input signal), a second pipe (sensor output airflow), and a third pipe (output air signal of batch end information/cleaning button). More specifically, the number of day-old chicks to be vaccinated can be selected. The number of day old chicks selected to be vaccinated can be based on the capacity of crates at a hatchery. For example, some crates may contain 100 chicks, 50 chicks, 75 chicks, etc. For example, if the number of day old chicks to be vaccinated is selected as 75, at each activation, the head of the chick contacts the action button 105, which can trigger one or more of the first, second, or third pipe. More specifically, air in the first pipe can pass to the second pipe, which can start the vaccination cycle. When the operator vaccinates the $75^{th}$ day old chick, the vaccination device stops and air can be sent through the third pipe to signal the end of batch, and the vaccination device can be prevented from vaccinating the $76^{th}$ day old chick. During this time, the crate can be changed and the vaccination device can reset. While the crate is being changed, air can still be present in the third pipe. This can have a dual-function including notifying the operator to change the crate and notifying the operator to clean the back of the action button 105 between the action button and the first outer surface 110 and the second outer surface 115. The third pipe can be positioned behind a back face of the action button 105 and can blow away debris and residue (e.g., fluff, dust, feathers, vaccine, etc.), which may have built up during the previous vaccinations.

Figure 3:
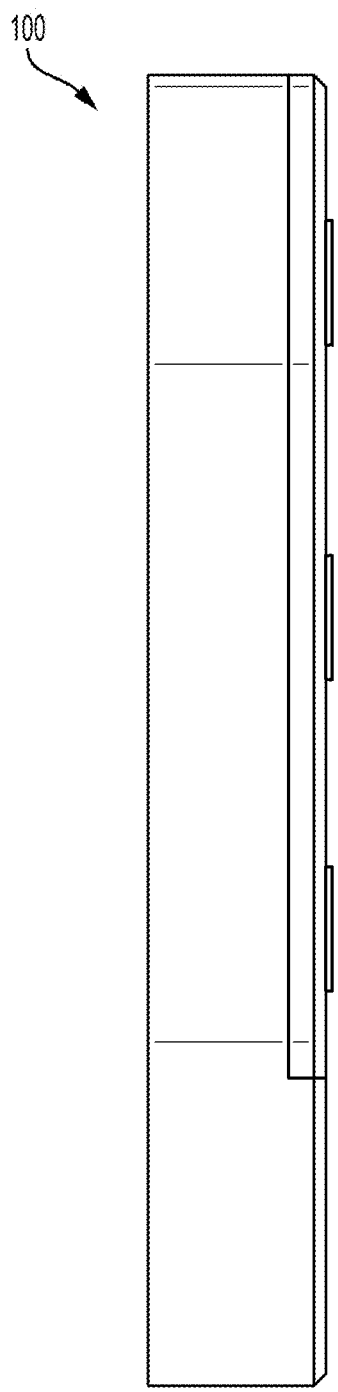
FIG. 3 depicts an exemplary left side view of an action plate according to one or more aspects of the disclosed subject matter.

FIG. 3 depicts an exemplary left side view of the action plate 100 according to one or more aspects of the disclosed subject matter.

Figure 4:
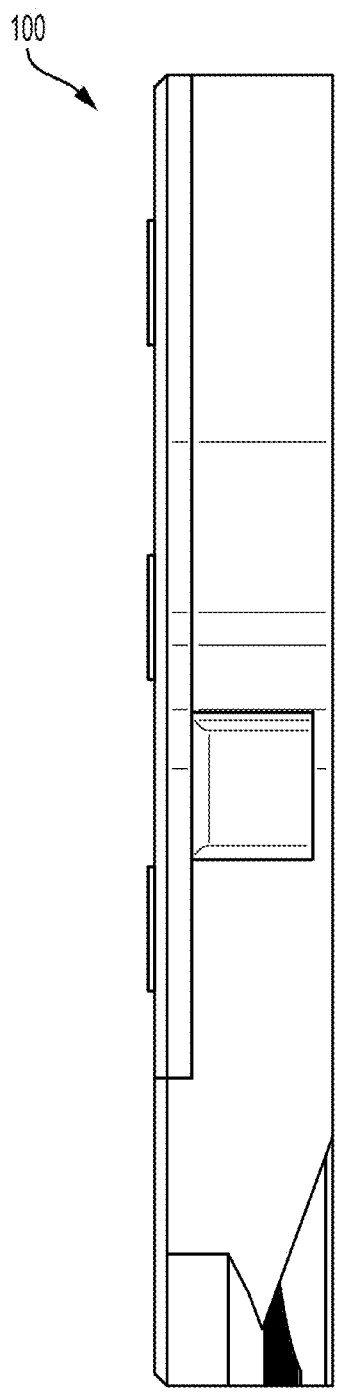
FIG. 4 depicts an exemplary right side view of an action plate according to one or more aspects of the disclosed subject matter.

FIG. 4 depicts an exemplary right side view of the action plate 100 according to one or more aspects of the disclosed subject matter.

Figure 5:
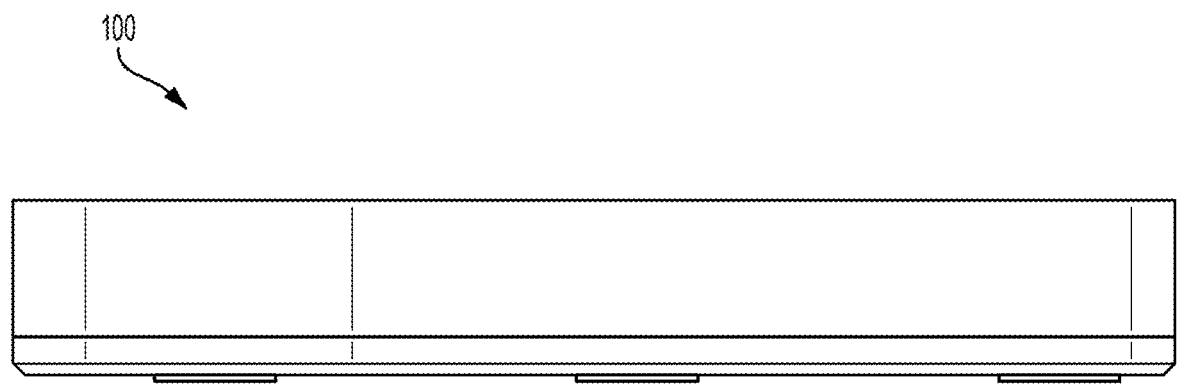
FIG. 5 depicts an exemplary upper side view of an action plate according to one or more aspects of the disclosed subject matter.

FIG. 5 depicts an exemplary upper side view of the action plate 100 according to one or more aspects of the disclosed subject matter.

Figure 6:
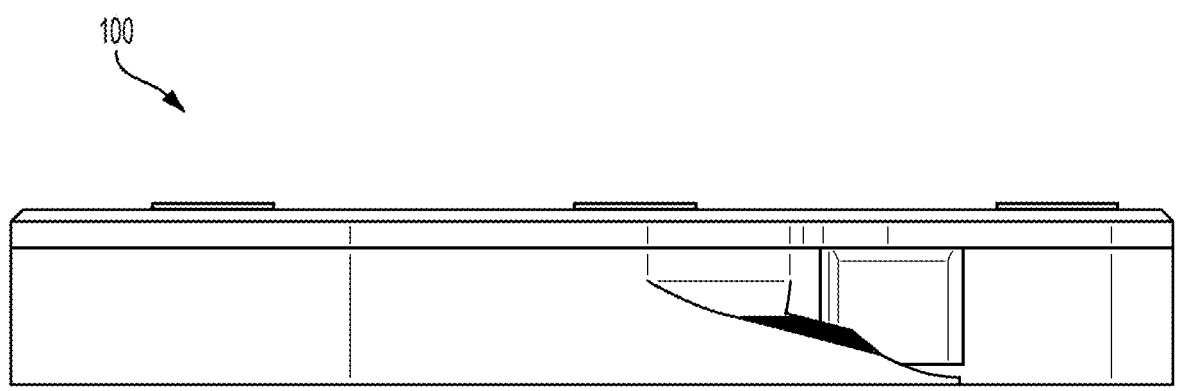
FIG. 6 depicts an exemplary lower side view of an action plate according to one or more aspects of the disclosed subject matter.

FIG. 6 depicts an exemplary lower side view of the action plate 100 according to one or more aspects of the disclosed subject matter.

Figure 7:
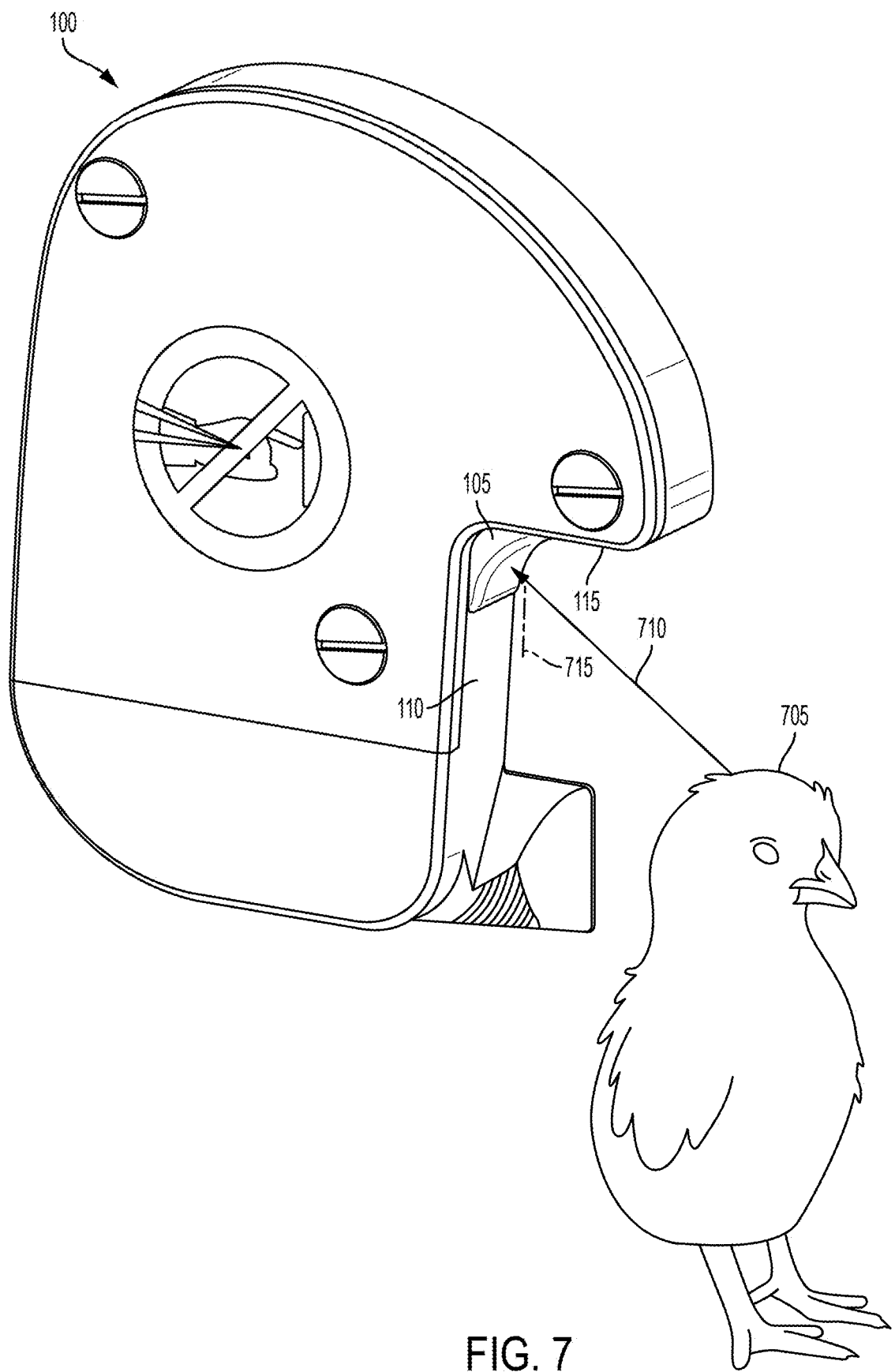
FIG. 7 depicts an exemplary vaccination technique for an action plate according to one or more aspects of the disclosed subject matter.
Figure 10:
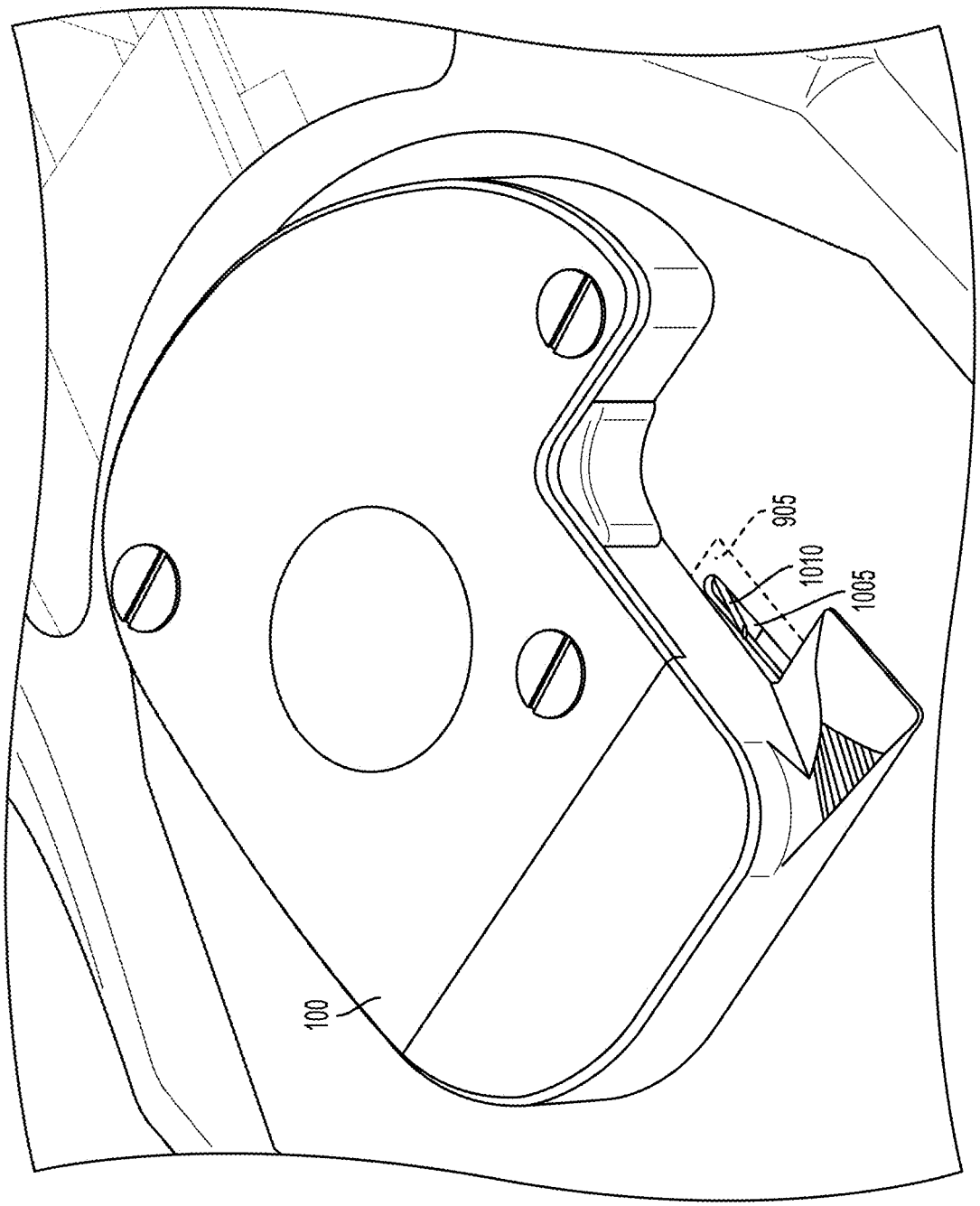
FIG. 10 depicts an exemplary perspective view of an action plate according to one or more aspects of the disclosed subject matter.

FIG. 7 depicts an exemplary vaccination technique for the action plate 100 according to one or more aspects of the disclosed subject matter. The activation technique can include loading and then pressing a day-old chick 705 in a direction corresponding to arrow 710. The arrow 710 can correspond to an activation axis for the action button 105. For example, a predetermined minimum force can be applied at least substantially in the direction of arrow 710 to press and/or activate the action button 105 such that a force greater than or equal to the minimum amount of force can press the action button 105. The amount of force required to press the action button 105 can be between 1 and 3 Newtons. The activation axis (i.e., arrow 710) can divide the first outer surface 110 and the second outer surface 115 such that the first outer surface 110 and the second outer surface 115 connect at the activation axis, for example. Pressing the action button 105 can cause a vaccination to be delivered to the day-old chick 705. The vaccination can be delivered via a vaccination needle extending from a hole in a vaccination device (FIG. 10). The action button 105 can be configured to receive the day-old chick 705 in a position that provides high quality and efficacy for each vaccination, as well as improved safety for the operator and the day-old chick 705. The arrow 710 can correspond to a direction that the operator applies force, using a finger, for example. The force can be applied at a predetermined angle away from the vaccination needle (e.g., vaccination needle 1010 in FIG. 10) that delivers the vaccination along a vaccination delivery location axis 715. The angle created by the activation axis 710 and the axis 715 can be 45 degrees. The risk of self-injection can be reduced because the action button 105 is located the predetermined distance away from the vaccination delivery area, but also because the force can be applied in a direction corresponding to a predetermined angle away from a vaccination delivery location. The vaccination delivery location can be an area where the vaccination needle extends from an opening in a vaccination device to inject the day-old chick 705. The predetermined angle can be based on the direction of arrow 710 and axis 715. Arrow 710 may correspond to an axis on which the action button 105 is pressed. Axis 715 may be an axis at least substantially parallel to the first outer surface 110. Alternatively, or additionally, axis 715 may be an axis corresponding to an opening in the vaccination device that houses the vaccination needle.

It should be appreciated that the action button 105 may be activated based on a range of angles relative to the activation axis. For example, if the action button 105 is pressed 10 degrees off-axis relative to the activation axis, the action button 105 may still be able to be pressed. As a result, presenting the day-old chick to the action plate may still result in high quality and safe vaccination because the presentation is consistent even though the direction in which the day-old chick is being pressed toward the action button 105 may be 10 degrees off-axis, for example. However, attempting to press the action button in the direction of the activation axis may allow for an easier, and therefore faster, press of the action button 105.

Additionally, the shape of the action button 105 in combination with the first outer surface 110 and the second outer surface 115 can be configured to receive the day-old chick consistently in the same location. For example, the shape of the action button 105 can be concave to fit a crown of a head of the day-old chick. The first outer surface 110 and the second outer surface 115 can be flat and form a rounded corner in combination with the action button 105. As a result, the design of the action plate 100 and the location and shape of the action button 105 can be configured to provide consistent presentation (e.g., loading) of the day-old chicks. Further, consistent loading of the day-old chicks further improves the quality and efficacy of the vaccinations.

Figure 8:
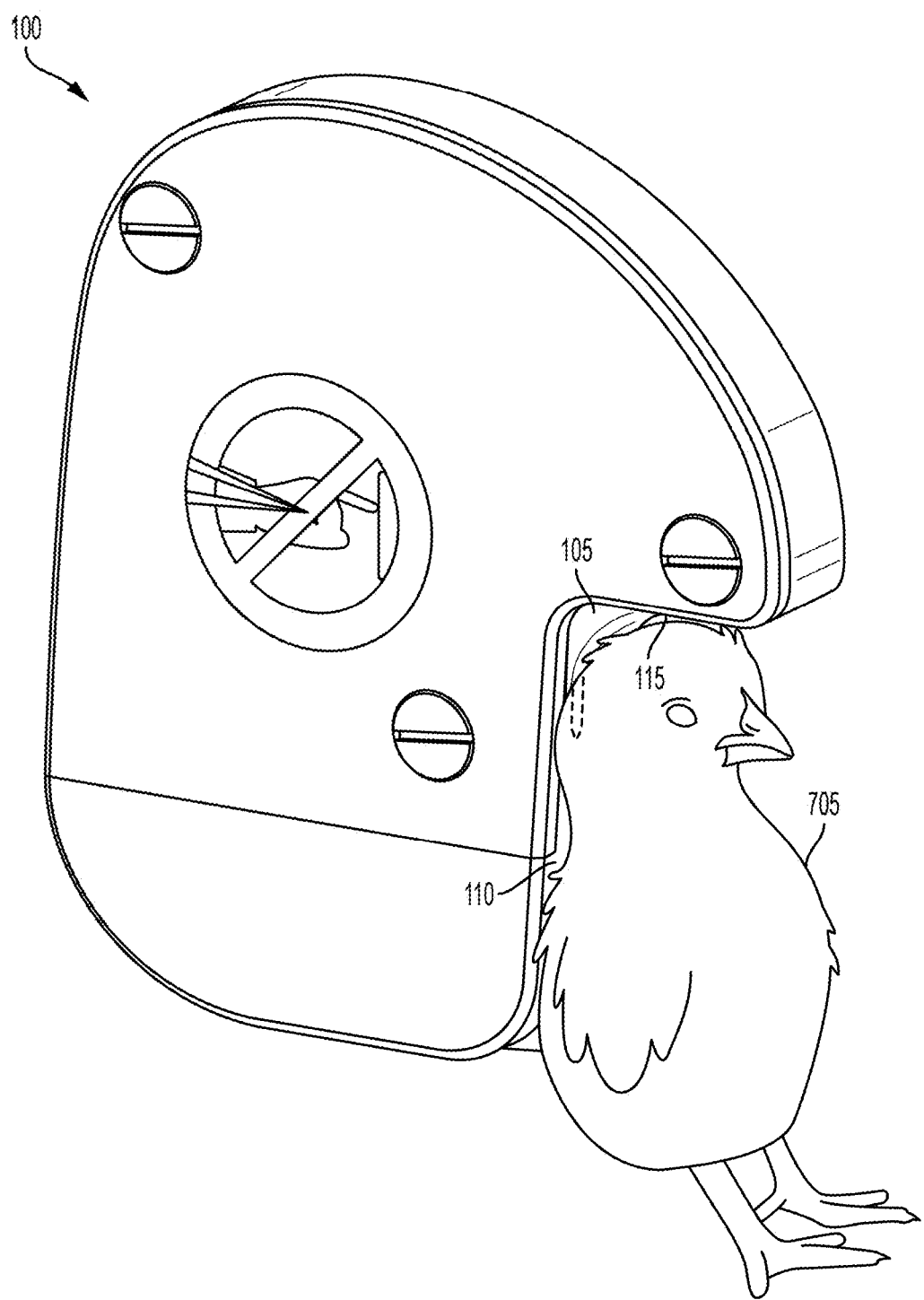
FIG. 8 depicts an exemplary vaccination position for an action plate according to one or more aspects of the disclosed subject matter.

FIG. 8 depicts an exemplary vaccination position for the action plate 100 according to one or more aspects of the disclosed subject matter. The vaccination position can include the day-old chick 705 loaded/presented in the action plate 100 such that the loading of the day-old chick 705 activates the action button 105 which can deliver the vaccination to the day-old chick with high quality and efficacy in a predetermined injection location, wherein the injection location can correspond to a subcutaneous injection in a neck of the day-old chick, for example. The design of the action plate 100 and the location of the action button 105 can consistently receive the day-old chick 705 such that the day-old chick 705 is consistently loaded into the action plate in the same position. More specifically, a head of the day-old chick 705 can form to the curve of the action button 105. The crown of the head of the day-old chick 705 can be placed against the second outer surface 115 such that the day-old chick 705 cannot be positioned past the second outer surface 115. Similarly, the back of the day-old chick 705 can be positioned against the first outer surface 110 such that the day-old chick 105 cannot be positioned past the first outer surface 110. The design of the action plate 100 and the location of the action button 105 can additionally be responsible for allowing operators to maintain the vaccination speed they may be accustomed too while maintain the safety of the operator and the day-old chick 705, as well as the quality and efficacy of the vaccinations.

Figure 9:
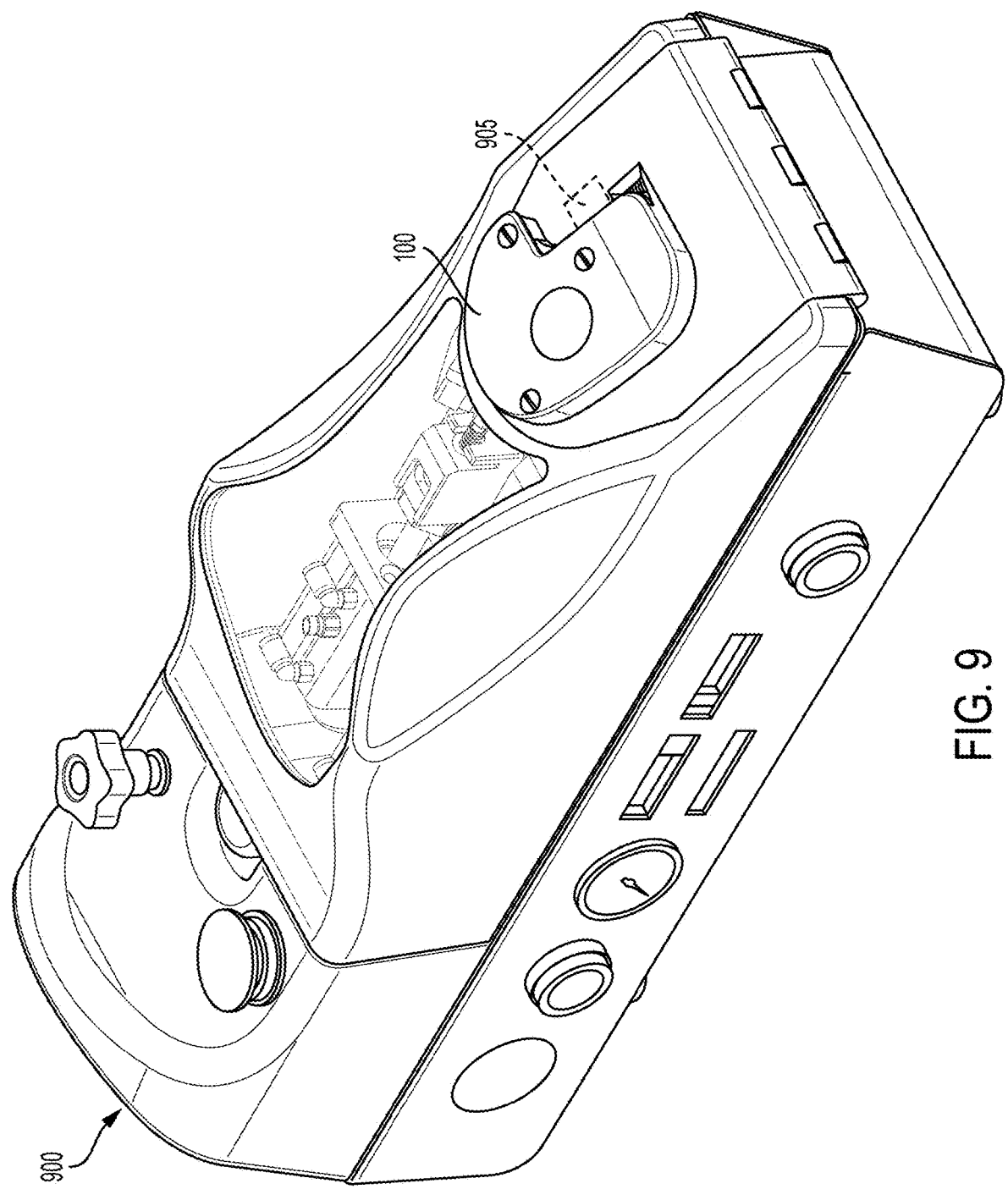
FIG. 9 depicts an exemplary perspective view of a vaccination device according to one or more aspects of the disclosed subject matter.

FIG. 9 depicts an exemplary perspective view of a vaccination device 900 according to one or more aspects of the disclosed subject matter. The vaccination device 900 can include the activation plate 100 and a vaccination delivery area 905. The vaccination device 900 can include various components to store and provide the vaccination for delivery. For example, internal components of the vaccination device 900 can connect to the connection points 205 to assist in delivering the correct dose of the vaccination, for example. Additionally, the vaccination device 900 can assist in the operation of a detection valve which can be configured to mechanically trigger the vaccination needle (e.g., vaccination needle 1010 in FIG. 10) when the action button 105 is pressed.

FIG. 10 depicts an exemplary perspective view of the action plate 100 according to one or more aspects of the disclosed subject matter. The action plate 100 can be secured to a surface of the vaccination device 900. The vaccination delivery area 905 can include an opening 1005 in the vaccination device 900 from which a vaccination needle 1010 can extend when activated via the action button 105 to deliver a vaccination via an injection. The injection can be a subcutaneous injection in a neck of the day-old chick 705, for example. The opening 1005 can be positioned at a predetermined angle relative to the activation axis, wherein the activation axis can correspond to the arrow 710. Additionally, the vaccination delivery area 905 can be positioned a predetermined distance from the first outer surface 110. The predetermined distance between the delivery area 905 and the first outer surface 110 can be between 1 and 2 millimeters for subcutaneous injection. The action plate may be adjustable to adapt to the size of the needle and the size of the day old chick.

The vaccination needle 1010 can be positioned relative to the action button. For example, the axis of the vaccination needle 1010 can make an angle of 4 relative to the first outer surface 110. A distance between a low end of the action button 110 (e.g., the end of the action button adjacent to the outer surface 110) and the vaccination delivery area 905 can be about 7 millimeters (as displayed in FIG. 12) and the distance from the middle of the action button can be about 14 millimeters (as displayed in FIG. 11). It should be appreciated that the measurements can also be made from the opening 1005 in the vaccination delivery area 905. The distance between the vaccination needle 1010 and the first outer surface 110 can be 1.3 millimeters±0.3 millimeters. The vaccination needle 1010 may extend from the opening 1005 a distance of 20.5 millimeters±0.5 millimeters. The tip of the vaccination needle can be 5 millimeters above the base to which the action plate is attached. The vaccination needles can be various diameters based on the volume of vaccination to be injected. In addition, the vaccination needle 905 can be various lengths. As a result, the position of the action plate can be adjustable to accommodate the various relative measurements as described herein.

Figure 11:
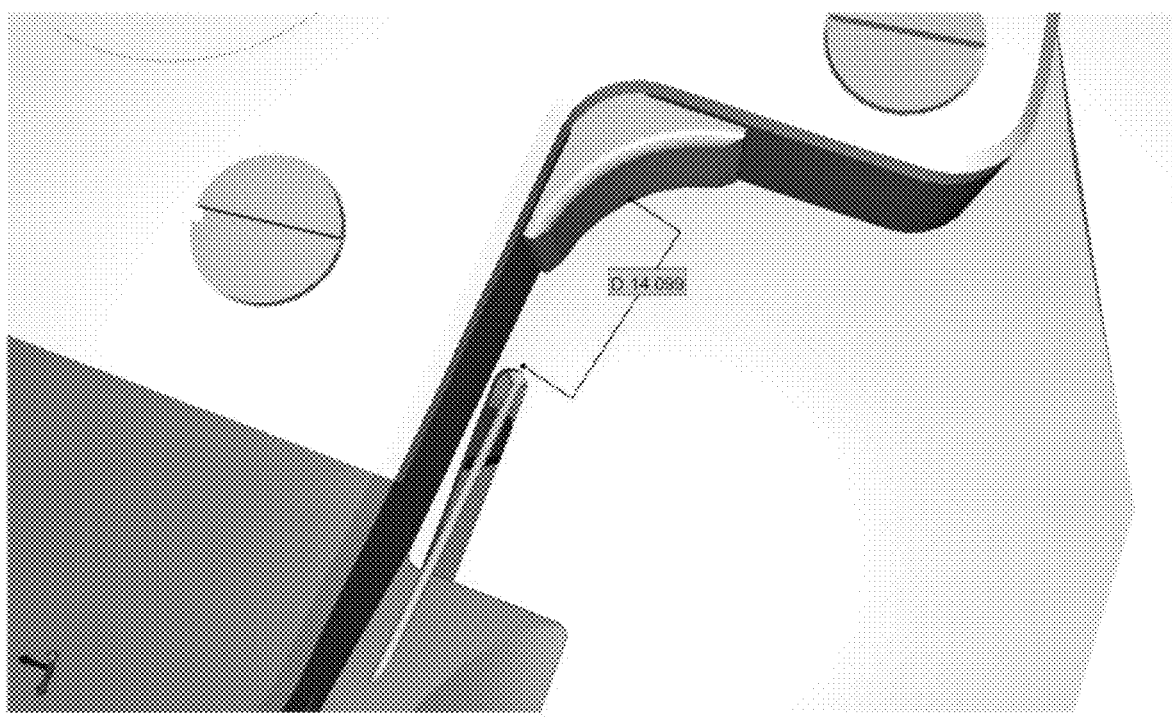
FIG. 11 depicts an exemplary distance from a middle of an action button to a vaccination delivery area according to one or more aspects of the disclosed subject matter.

FIG. 11 depicts an exemplary distance from a middle of an action button (e.g., action button 105) to a vaccination delivery area (e.g., vaccination delivery area 905) according to one or more aspects of the disclosed subject matter.

Figure 12:
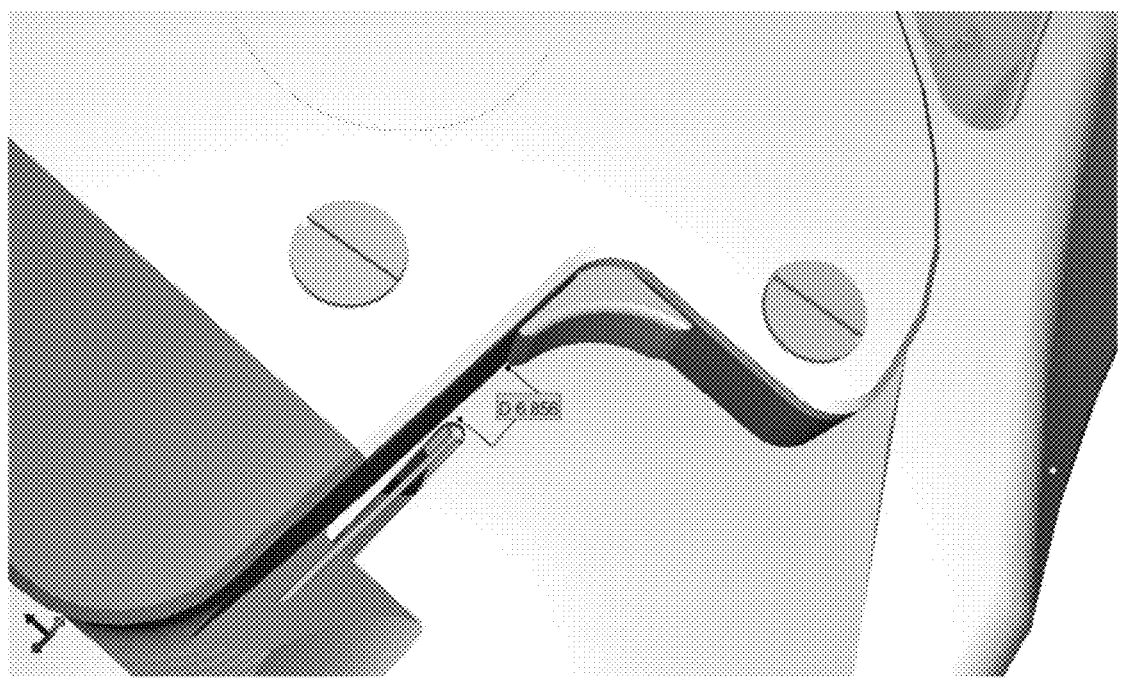
FIG. 12 depicts an exemplary distance form a lower portion of an action button to a vaccination delivery area according to one or more aspects of the disclosed subject matter.

FIG. 12 depicts an exemplary distance form a lower portion of an action button (e.g., action button 105) to a vaccination delivery area (e.g., vaccination delivery area 905) according to one or more aspects of the disclosed subject matter.

Having now described embodiments of the disclosed subject matter, it should be apparent to those skilled in the art that the foregoing is merely illustrative and not limiting, having been presented by way of example only. Thus, although particular configurations have been discussed herein, other configurations can also be employed. Numerous modifications and other embodiments (e.g., combinations, rearrangements, etc.) are enabled by the present disclosure and are within the scope of one of ordinary skill in the art and are contemplated as falling within the scope of the disclosed subject matter and any equivalents thereto. Features of the disclosed embodiments can be combined, rearranged, omitted, etc., within the scope of the invention to produce additional embodiments. Furthermore, certain features may sometimes be used to advantage without a corresponding use of other features. Accordingly, Applicant(s) intend(s) to embrace all such alternatives, modifications, equivalents, and variations that are within the spirit and scope of the disclosed subject matter.

The invention claimed is:

1. A vaccination system, comprising:
a vaccination device;
a vaccination needle configured to extend from the vaccination device at a vaccination delivery location; and
an action plate coupled to the vaccination device, the action plate being positioned at a predetermined location relative to the vaccination delivery location, wherein the action plate includes
an action button positioned where a first outer surface of the action plate connects to a second outer surface of the action plate, wherein the action button is configured to
receive a predetermined amount of force along an activation axis of the action button, wherein the predetermined amount of force is configured to press the action button, and
in response to pressing the action button, cause the vaccination needle to extend from the vaccination device at the vaccination delivery location to deliver a subcutaneous injection at an injection location,
wherein the first outer surface and the second outer surface connect at the activation axis.

2. The vaccination system of claim 1, wherein the predetermined amount of a force is greater than or equal to a minimum amount of force that activates the action button.

3. The vaccination system of claim 1, wherein at least a first portion of the action plate is anodized aluminum and at least a second portion is made from plastic.

4. The vaccination system of claim 1, wherein the activation axis creates a first predetermined angle relative to the first outer surface, the first predetermine angle being configured to position an operator's hand a predetermined distance away from the vaccination delivery location.

5. The vaccination system of claim 4, wherein the vaccination delivery location is spaced apart from the action button.

6. The vaccination system of claim 5, wherein the vaccination delivery location includes an opening in the vaccination device from which the vaccination needle extends, the opening in the vaccination device being positioned at a predetermined angle relative to the activation axis.

7. The vaccination system of claim 1, wherein the first outer surface and the second outer surface connect to form a corner and the action button projects outwardly from the corner.

8. A vaccination system, comprising:
a vaccination device including a vaccination needle; and
an action plate, comprising:
a first outer surface and a second outer surface that connect to form a corner; and
an action button positioned a predetermined distance away from a vaccination delivery location, wherein the action button is configured to
receive a predetermined amount of force along an activation axis of the action button, wherein the predetermined amount of force is configured to press the action button, and
in response to pressing the action button, cause the vaccination needle to extend from the vaccination device at a vaccination delivery location to deliver a subcutaneous injection at an injection location,
wherein the first outer surface and the second outer surface of the action plate connect at the activation axis.

9. The vaccination system of claim 8, wherein the predetermined distance is approximately 14 millimeters from a center of the action button to the vaccination delivery location.

10. The vaccination system of claim 8, wherein the predetermined amount of a force is greater than or equal to a minimum force of 1 Newton.

11. The vaccination system of claim 8, wherein at least a portion of the action plate is made from anodized aluminum and at least a portion of the action plate is made from plastic.

12. The vaccination system of claim 8, wherein the activation axis creates a predetermined angle relative to the first outer surface of the action plate.

13. The vaccination system of claim 12, wherein the vaccination delivery location is spaced apart from the first outer surface of the action plate.

14. The vaccination system of claim 13, wherein the vaccination delivery location includes an opening in the vaccination device from which the vaccination needle extends, the opening in the vaccination device being positioned at a predetermined angle relative to the activation axis.

15. The vaccination system of claim 8, wherein the action button projects outwardly from the corner.

16. A method for vaccination, comprising:
- receiving a predetermined amount of force along an activation axis of an action button, the action button being positioned in a corner formed by a first outer surface and a second outer surface on an action plate, wherein the predetermined amount of force is configured to press the action button; and
- in response to pressing the action button, causing a vaccination needle to extend from the vaccination device at a vaccination delivery location to deliver a subcutaneous injection at an injection location,
- wherein the first outer surface and the second outer surface of the action plate connect at the activation axis.

17. The method of claim 16, wherein the predetermined location of the action button on the action plate is positioned relative to the vaccination delivery location, the activation axis of the action button being at a predetermined angle relative to a vaccination delivery location axis.

18. The method of claim 16, wherein the vaccination delivery location is spaced apart from the first outer surface.

19. The method of claim 18, wherein the vaccination delivery location is positioned between 1 and 2 millimeters from the first outer surface.

20. The method of claim 16, wherein a center of the action button is positioned approximately 14 millimeters from the vaccination delivery location.

21. The method of claim 16, wherein the action button projects outwardly from the corner.

* * * * *